US00PP19706P2

(12) United States Plant Patent
Psenner

(10) Patent No.: US PP19,706 P2
(45) Date of Patent: Feb. 10, 2009

(54) *LANTANA* PLANT NAMED '2003.301'

(50) Latin Name: *Lantana camara*
Varietal Denomination: 2003.301

(75) Inventor: Thomas Psenner, Bozen (IT)

(73) Assignee: Amerinova Properties LLC, Bonsall, CA (US)

( * ) Notice: Subject to any disclaimer, the term of this patent is extended or adjusted under 35 U.S.C. 154(b) by 0 days.

(21) Appl. No.: 11/983,723

(22) Filed: Nov. 12, 2007

(51) Int. Cl.
*A01H 5/00* (2006.01)

(52) U.S. Cl. ..... Plt./227
(58) Field of Classification Search ..... Plt./227
See application file for complete search history.

*Primary Examiner*—Annette H Para
*Assistant Examiner*—June Hwu
(74) *Attorney, Agent, or Firm*—C. A. Whealy

(57) ABSTRACT

A new and distinct cultivar of *Lantana* plant named '2003.301', characterized by its compact and upright plant habit; freely branching growth habit; relatively small leaves; freely flowering habit; and large red-colored flowers that are held above and beyond the foliage.

1 Drawing Sheet

Botanical designation: *Lantana camara.*
Cultivar denomination: '2003.301'.

BACKGROUND OF THE INVENTION

The present invention relates to a new and distinct cultivar of *Lantana,* botanically known as *Lantana camara,* and hereinafter referred to by the name '2003.301'.

The new *Lantana* is a product of a planned breeding program conducted by the Inventor in Bozen, Italy. The objective of the breeding program is to create new compact freely-branching *Lantana* cultivars with attractive flower coloration.

The new *Lantana* originated from a cross-pollination made by the Inventor in 2002 in Bozen, Italy of the *Lantana camara* cultivar Mini Yellow, not patented, as the female, or seed, parent with a proprietary selection of *Lantana camara* identified as code number 2000#12, not patented, as the male, or pollen, parent. The new *Lantana* was discovered and selected by the Inventor as a single flowering plant within the progeny of the stated cross-pollination in a controlled environment in Bozen, Italy in 2003.

Asexual reproduction of the new *Lantana* by vegetative cuttings in a controlled environment in Bozen, Italy since May, 2003, has shown that the unique features of this new *Lantana* are stable and reproduced true to type in successive generations.

SUMMARY OF THE INVENTION

The cultivar 2003.301 has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of '2003.301'. These characteristics in combination distinguish '2003.301' as a new and distinct cultivar of *Lantana:*

1. Compact and upright plant habit.
2. Freely branching growth habit.

3. Relatively small leaves.
4. Freely flowering habit.
5. Large red-colored flowers that are held above and beyond the foliage.

Plants of the new *Lantana* can be compared to plants of the female parent, the cultivar Mini Yellow. Plants of the new *Lantana* differ from plants of the cultivar Mini Yellow in the following characteristics:

1. Plants of the new *Lantana* are more upright than plants of the cultivar Mini Yellow.
2. Plants of the new *Lantana* flower earlier than plants of the cultivar Mini Yellow.
3. Plants of the new *Lantana* have larger flowers than plants of the cultivar Mini Yellow.
4. Plants of the new *Lantana* and the cultivar Mini Yellow differ in flower color as plants of the cultivar Mini Yellow have yellow-colored flowers.

Plants of the new *Lantana* can be compared to plants of the male parent selection. Plants of the new *Lantana* differ from plants of the male parent selection in the following characteristics:

1. Plants of the new *Lantana* are more compact than plants of the male parent selection.
2. Plants of the new *Lantana* have smaller leaves than plants of the male parent selection.
3. Plants of the new *Lantana* and the male parent selection differ in flower color as plants of the male parent selection have dark yellow/orange-colored flowers.

Plants of the new *Lantana* can be compared to plants of the *Lantana* cultivar Goldsonne, not patented. Plants of the new *Lantana* differ from plants of the cultivar Goldsonne in the following characteristics:

1. Plants of the new *Lantana* are more compact than plants of the cultivar Goldsonne.
2. Plants of the new *Lantana* have shorter internodes than plants of the cultivar Goldsonne.
3. Plants of the new *Lantana* have smaller leaves than plants of the cultivar Goldsonne.

BRIEF DESCRIPTION OF THE PHOTOGRAPHS

The accompanying colored photographs illustrate the overall appearance of the new *Lantana,* showing the colors as true as it is reasonably possible to obtain in colored reproductions of this type. Colors in the photographs may differ slightly from the color values cited in the detailed botanical description which accurately describe the colors of the new *Lantana*.

The photograph at the bottom of the sheet comprises a side perspective view of a typical flowering plant of '2003.301' grown in a container.

The photograph at the top of the sheet is a close-up view of typical inflorescences and leaves of '2003.301'.

DETAILED BOTANICAL DESCRIPTION

The aforementioned photographs and following observations and measurements describe plants grown in Bonsall, Calif., under commercial practice during the spring and summer in an outdoor nursery with day temperatures ranging from 13° C. to 38° C. and night temperatures ranging from 10° C. to 24° C. Plants used in the photographs and for the description were grown in containers for about three months. In the following description, color references are made to The Royal Horticultural Society Colour Chart, 1995 Edition, except where general terms of ordinary dictionary significance are used.

Botanical classification: *Lantana camara* cultivar 2003.301.

Parentage:

*Female, or seed, parent.*—*Lantana camara* cultivar Mini Yellow, not patented.

*Male, or pollen, parent.*—Proprietary selection of *Lantana camara* identified as code number 2000#12, not patented.

Propagation:

*Type.*—By vegetative cuttings.

*Time to initiate roots, summer.*—About 10 days at 27° C.

*Time to initiate roots, winter.*—About 15 days at 24° C.

*Time to produce a rooted young plant.*—About 37 days at 29° C.

*Root description.*—Fibrous; thin; white in color.

*Rooting habit.*—Freely branching; dense.

Plant description:

*Plant habit.*—Compact and upright plant habit. Freely branching habit with about four to five lateral branches per plant; pinching enhances lateral branch development. Moderately vigorous growth habit.

*Plant height.*—About 25 cm.

*Plant diameter.*—About 24 cm by 26 cm.

Lateral branch description:

*Length.*—About 23 cm.

*Diameter.*—About 3.5 mm.

*Internode length.*—About 2.7 cm.

*Strength.*—Strong.

*Texture.*—Pubescent; coarse.

*Color.*—146B.

Foliage description:

*Arrangement.*—Opposite, simple.

*Length.*—About 4.7 cm.

*Width.*—About 3 cm.

*Shape.*—Elliptic to ovate.

*Apex.*—Acute.

*Base.*—Obtuse.

*Margin.*—Serrate to crenate.

*Texture, upper and lower surfaces.*—Pubescent; coarse, rough.

*Venation pattern.*—Pinnate; arcuate.

*Color.*—Developing and fully expanded foliage, upper surface: 147A; venation, 146C. Developing and fully expanded foliage, lower surface: 147B; venation, 147C.

*Petiole.*—Length: About 6 mm. Diameter: About 1.5 mm. Texture, upper and lower surfaces: Pubescent. Color, upper and lower surfaces: 146B.

Flower description:

*Flower arrangement and habit.*—Solitary tubular flowers arranged in hemispherical axially umbels; flowers face mostly upward or outward; flowers sessile. Freely flowering habit with potentially two inflorescences developing per node, each umbel with about 30 flowers.

*Natural flowering season.*—Spring until frost in the autumn; flowering continuous during this period.

*Flower longevity on the plant.*—About four to five days. Flowers not persistent.

*Fragrance.*—Faint; grapefruit-like.

*Inflorescence height.*—About 1.8 cm.

*Inflorescence diameter.*—About 3 cm.

*Flowers.*—Appearance: Flared trumpet, corolla fused, four-parted. Diameter: About 7 mm by 9 mm. Depth (height): About 1.7 cm. Tube diameter: About 2 mm.

*Flower buds.*—Length: About 1.1 cm. Diameter: About 3 mm. Shape: Elongate, oblong. Color: Towards the apex, 45A; towards the base, 23B.

*Corolla.*—Arrangement: Single whorl of four fused petals. Petal lobe length: About 2 mm to 4 mm. Petal lobe width: About 3 mm to 4 mm. Petal lobe shape: Rounded. Petal lobe apex: Rounded. Petal margin: Entire, slightly sinuate. Petal texture, upper surface: Smooth, glabrous. Petal texture, lower surface: Pubescent. Color: When opening, upper surface: 17B; towards the margins, 33A. When opening, lower surface: 16B. Fully opened, upper surface: With development, color shifts from 26A, to 28A, to 42A and to eventually 46A. Fully opened, lower surface: With development, color shifts from 31A to 31B, to 34B to 34C, to 42B and to eventually 46A to 46B. Corolla tube: With development, color shifts from 28C, to 34B to 34C and to eventually 45D.

*Calyx.*—Appearance: Short and narrow tubular calyx. Length: About 2 mm. Diameter: About 1 mm. Sepal apex: Acute. Sepal margin: Entire. Sepal texture, inner surface: Smooth, glabrous. Sepal texture, outer surface: Pubescent. Sepal color, inner surfaces: 145C. Sepal color, outer surface: 145A.

*Peduncles.*—Length: About 3.2 cm to 3.6 cm. Diameter: About 1 mm. Strength: Strong. Texture: Pubescent. Color: 147B.

*Reproductive organs.*—Stamens: Quantity/arrangement: Four per flower, adnate to floral tube. Filament length: About 2 mm. Filament color: 10A. Anther shape: Oval. Anther length: Less than 1 mm. Anther color: 12B. Pollen amount: Scarce. Pollen color: 12B. Pistils: Quantity: One per flower. Pistil length: About 4 mm. Stigma shape: Rounded. Stigma color: 145B. Style length: About 2.5 mm. Style color: 145C. Ovary color: 145A.

*Fruits/seed.*—Fruit and seed development have not been observed.

Garden performance: Plants of the new *Lantana* have been observed to have good garden performance and to tolerate wind, rain and temperatures ranging from about 1° C. to about 38° C.

Pathogen/pest resistance: Plants of the new *Lantana* have not been observed to be resistant to pests and pathogens common to *Lantanas*.

It is claimed:

1. A new and distinct *Lantana* plant named '2003.301' as illustrated and described.

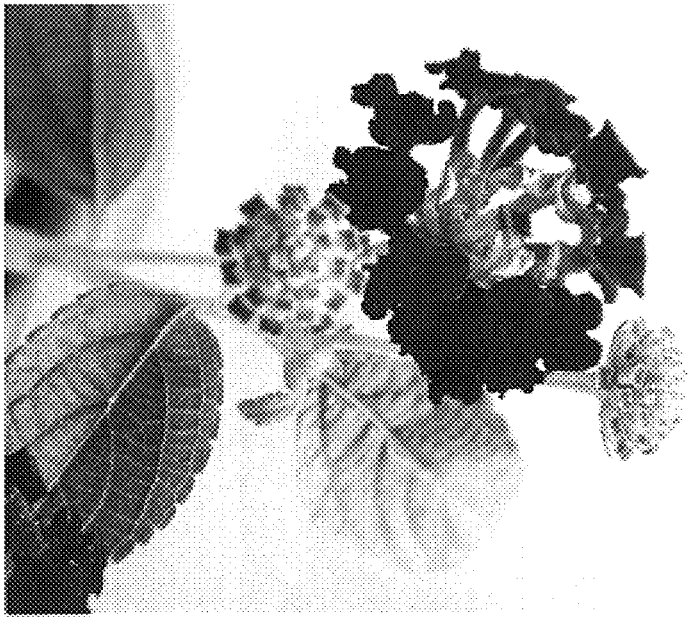
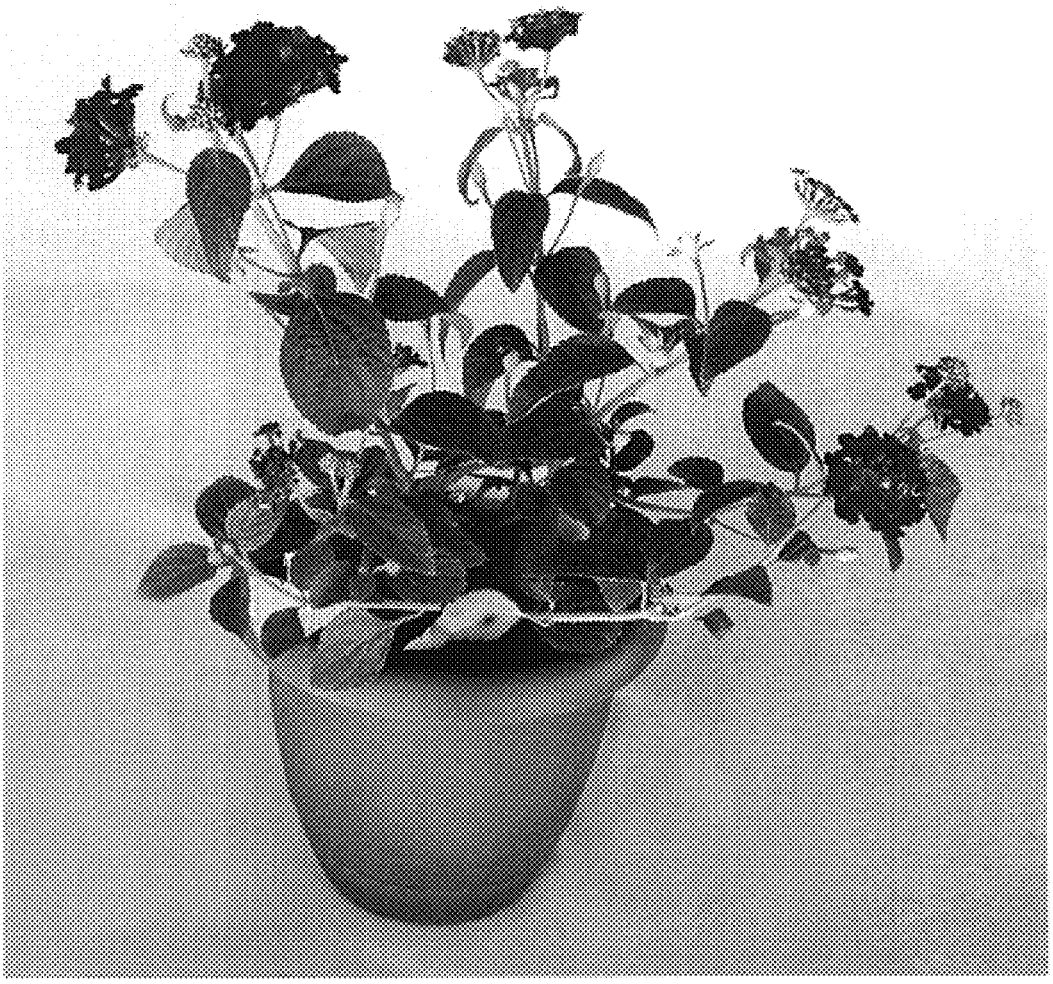

* * * * *